United States Patent [19]

Kim et al.

[11] Patent Number: 5,750,680
[45] Date of Patent: May 12, 1998

[54] N-VINYLLACTAM DERIVATIVES AND POLYMER THEREOF

[75] Inventors: Jin Baek Kim; Min Ho Jung; Kyeong Ho Chang, all of Seoul, Rep. of Korea

[73] Assignees: Hyundai Electronics Industries Co., Ltd.; Korea Advanced Institute of Science & Technology, both of Rep. of Korea

[21] Appl. No.: 713,085

[22] Filed: Sep. 12, 1996

[30] Foreign Application Priority Data

Sep. 14, 1995 [KR] Rep. of Korea ............ 95 30063

[51] Int. Cl.$^6$ ............ C07F 7/10; C08F 30/08; G03C 1/60
[52] U.S. Cl. ............ 540/200; 540/354; 540/358; 540/252; 540/463; 540/451; 540/485; 540/487; 540/524; 540/525; 540/526; 540/531; 546/14; 546/21; 546/243; 548/110; 548/111; 548/544; 548/545; 548/551; 525/326.9
[58] Field of Search ............ 540/200, 354, 540/358, 452, 463, 451, 485, 487, 524, 525, 526, 531; 546/14, 21, 243; 548/110, 111, 544, 545, 551

[56] References Cited

U.S. PATENT DOCUMENTS 4,115,128 9/1978 Kita .................. 96/91 D
4,491,628 1/1985 Ito et al. ............ 430/176

*Primary Examiner*—Robert T. Bond
*Attorney, Agent, or Firm*—Gary M. Nath; Nath & Associates; Patricia Drost

[57] ABSTRACT

N-vinyllactam derivatives protected at the 3-position are provided and represented by the following formula (I). These are polymerized into homo- and copolymers for use in microlithography of semiconductor manufacture. The polymers are used as a photoresist material suitable for a deep UV process so that pictures of high sensitivity and high resolution can be obtained. In addition, ultrafine circuits can be formed and an exceptional improvement in pattern formation can be accomplished through the use of the photoresist of the invention.

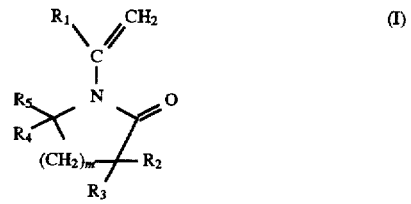

2 Claims, No Drawings

N-VINYLLACTAM DERIVATIVES AND POLYMER THEREOF

BACKGROUND OF THE INVENTION

1. Field of the Invention

The present invention relates to novel N-vinyllactam derivatives and polymers thereof for use in microlithography. More particularly, the present invention relates to N-vinyllactam derivatives and polymers thereof, used as materials for photoresist which is capable of forming picture of high sensitivity and high resolution by use of deep UV and to homo- and copolymers thereof for use as photoresist.

2. Description of the Prior Art

Usually, photoresist consists mainly of an alkali-soluble phenol-(or cresol-)formaldehyde novolak resin and a substituted naphthoquinone diazide compound as a photosensitive material (photoactive ingredient), as described in U.S. Pat. Nos. 3,666,473, 4,115,128 and 4,173,470.

While the novolak resin used in such photoresist is dissolved in an aqueous alkali solution, the naphthoquinone photosensitive material acts as a dissolution inhibitor of resist. However, when a substrate coated with the photoresist is selectively subjected to chemical radiation, the photosensitive agent is induced to suffer from such structural modification that the exposed region of the photoresist coating is of stronger solubility to alkali than the unexposed region. By virtue of such differences in solubility, a relief pattern can be carved on the coating of the substrate. That is, when the substrate is immersed in an alkaline developing solution, the exposed region of the photoresist coating is dissolved whereas the unexposed region is not substantially affected, forming a pattern. However, the above-mentioned novolak type resists were not found to be suitable to the steper utilizing shorter wavelength, which will be used in the future, because they show high optical absorbance in the range of deep ultraviolet light, 200 to 300 nm.

In order to accomplish high sensitivity in the lithography process of semiconductor manufacture, chemical amplification resist has recently been developed. Indeed, the chemical amplification resist has been in the limelight since it was found to have the capacity for increasing sensitivity 100-fold over conventional positive novolak resists. Chemical amplification resist, which takes advantage of the photoacid generator (hereinafter referred to as "PAG"), is generally prepared by formulating PAG in a matrix polymer of a structure sensitively reacting to acid. For the mechanism of the photoreaction, when PAG is exposed to light or irradiated by a high energy beam, such as X-ray and electron beam, strong protonic acid, Bronsted acid, are generated, causing the main chain or the side chain of the matrix polymer to react toward decomposition, crosslinking or large change in polarity. This action of the acid induces, at the irradiated region, the solubility of the given developing solution to be altered. That is, increased or decreased. As a result, fine patterns can be formed.

Onium salt which is able to respond to light and radiation is known as the photoacid generator. Onium Salt typically includes ammonium salts, oxonium salts and sulfonium salts, etc. Recently, it has been reported that organic sulfonic ester can function as the photoacid generated.

Available for the matrix polymer, which can react with acid, is for example, polymers having a side chain such as t-butylester, t-butylcarbonate, t-butoxy or t-butoxycarbonyl groups, which can be decomposed into carboxylic acid, phenol or alcoholic functional group by acid. Among such side chain protecting groups, the t-butoxycarbonyl group is highest in sensitivity. Such acid-reactable polymer in a protected state or prior to reaction with acid, can be dissolved in an organic solvent but insoluble in an alkali aqueous solution. However, if the acid-reactable polymer is deprotected by reaction with acid, it is soluble in alkali aqueous solution because its polarity is significantly changed.

Using this principle, the development of chemical amplification resists has been a hot issue in recent years. T-Butoxycarbonyl-protected polyvinylphenol (hereinafter referred to as "t-bocPVP") is reported to be one of the most promising resins, as introduced in U.S. Pat. Nos. 4,491,628, 4,405,708 and 4,311,782.

A recent trend in submicrolithography is to use as a light source deep uv (wavelength 200 to 300 nm), preferably, a KrF excimer laser of high power (wavelength 248), rather than conventional uv, e.g., g-line (wavelength 436 nm) or i-line (wavelength 365 nm), in order to accomplish high sensitivity and high resolution. Therefore, the optical absorption of the matrix polymer should be minimized in the wavelength range of deep uv, particularly at 248 nm, the wavelength of KrF excimer laser. However, since t-bocPVP also contains the benzene group, it has the significant disadvantage of showing large optical absorption in short wavelength ranges.

SUMMARY OF THE INVENTION

Intensive research repeated by the present inventors aiming to develop a photoresist for submicrolithography which does not absorb deep uv in addition to having a high glass transition temperature necessary for processing procedure resulted in the finding that the chemical amplification resist polymerized with an alicyclic compound (N-vinyllactam) protected by an acid-reactable group is converted into an aqueous polymer when being deprotected and can thus be designed to form a pattern by using a weak alkali aqueous solution or pure water only, instead of strong alkali aqueous solution, thereby improving the pattern-forming processes considerably.

Therefore, it is a principal object of the present invention to provide an N-vinyllactam derivative monomer in which vinyllactam is blocked at the 3-position by various kinds of protecting groups, as a photoresist material for microlithography which satisfies high sensitivity and high resolution.

It is another object of the present invention to provide a polymer prepared from the monomer.

It is a further object of the present invention to provide a polymer for use in photoresist.

DETAILED DESCRIPTION OF THE INVENTION

The present invention provides a vinyllactam derivative monomer in which vinyllactam is protected at its 3-position. The monomer can be prepared by reacting vinyllactam with a strong base at low temperatures to give an enolate and introducing a protecting group into the 3-position of vinyllactam. Concrete examples of vinyllactam include N-vinylpyrrolidone, N-vinyl-4-butylpyrrolidone, N-vinyl-4-propylpyrrolidone, N-vinyl-4-ethylpyrrolidone, N-vinyl-4-methylpyrrolidone, N-vinyl-4-methyl-5-ethylpyrrolidone, N-vinyl-4-methyl-5-propylpyrrolidone, N-vinyl-5-methyl-5-ethylpyrrolidone, N-vinyl-5-propylpyrrolidone, N-vinyl-5-butylpyrrolidone, N-vinyl-5-piperidone, N-vinyl-4-methylpiperidone, N-vinyl-4-propylpiperidone, N-vinyl-4- butylpiperidone, N-vinyl-6-butylpiperidone, N-vinylcaprolactam, N-vinyl-4-methylcaprolactam, N-vinyl-6-methylcaprolactam, N-vinyl-6-propylcaprolactam, N-vinyl-7-butylcaprolactam and N-vinylimide. The strong base may be exemplified by t-butyllithium, sodium hydride and n-butyllithium. This monomer preparation is carried out in a solvent, examples include n-pentane, n-hexane, n-heptane, cyclohexane, ethylether and tetrahydrofuran. As the source of the protecting group, t-butylchloroformate, isobutylchloroformate, di(t-butyl)dicarbonate, methanesulfonylchloride, methanesulfonic anhydride, tetrahydropyran, 2-chlorotetrahydrofuran, trimethylsilylchloride, 4-methoxybenzylchloride, 4-nitrobenzylchloride, diethylisopropylsilylchloride and t-dimethylsilylchloride can be used.

The N-vinyllactam derivatives of the present invention are represented by the following general formula (I):

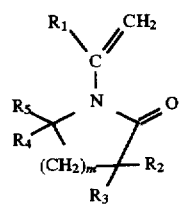

wherein, $R_1$ is hydrogen, an alkyl group containing 1 to 10 carbon atoms, an aryl group containing 6 to 12 carbon atoms or a trialkylsilyl group containing 3 to 9 carbon atoms;

$R_2$ represents —OR', —SO$_3$R', —CO$_2$R', —PO$_3$R', —SO$_2$R' or —PO$_2$R', wherein R' is an alkyl group containing 1 to 10 carbon atoms, a cycloalkyl group, containing 3 to 9 carbon atoms cyclo group containing a ring heteroatom such as N, O, P and S, or an aryl group containing 6 to 12 carbon atoms;

$R_3$ is hydrogen, an alkyl group containing 1 to 10 carbon atoms, an aryl group containing 6 to 12 carbon atoms, a trialkylsilyl group containing 3 to 9 carbon atoms, or $R_3$ is the same as $R_2$;

$R_4$ and $R_5$ is —OH, —OR, wherein R is an alkyl group containing 1 to 10 carbon atoms or an aryl group containing 6 to 12 carbon atoms, or R is the same as $R_1$; and m is an integer of 0 to 10.

By the method of the present invention, various monomers can be synthesized, including 3-(t-butoxycarbonyl)-1-vinyl-2-pyrrolidinone, 3-(t-butoxycarbonyl)-1-vinyl-4-butyl-2-pyrrolidinone, 3-(t-butoxycarbonyl)-1-vinyl-4-propyl-2-pyrrolidinone, 3-(tetrahydropyranyloxycarbonyl)-1-vinyl-2-pyrrolidinone, 3-(tetrahydropyranyloxycarbonyl)-1-vinyl-5-ethyl-2-pyrrolidinone, 3-(t-butoxycarbonyl)-1-vinyl-4-methyl-2-piperidone, 3-(t-butoxycarbonyl)-1-vinyl-4-propyl-2-piperidone, 3-(t-butoxycarbonyl)-1-vinyl-2-caprolactam, 3-(t-butoxycarbonyl)-1-vinyl-4-butyl-2-caprolactam, 3-(t-butoxycarbonyl)-1-vinyl-6-methyl-2-caprolactam, 3-(tetrahydropyranyloxycarbonyl)-1-vinyl-2-caprolactam, 3-(tetrahydropyranyloxycarbonyl)-1-vinyl-5-butyl-2-caprolactam, 3-(tetrahydropyranyloxycarbonyl)-1-vinyl-6-propyl-2-caprolactam, 3-(tetrahydrofuranyloxycarbonyl)-1-vinyl-2-pyrrolidinone, 3-(tetrahydrofuranyloxycarbonyl)-1-vinyl-4-butyl-2-pyrrolidinone, 3-(tetrahydrofuranyloxycarbonyl)-1-vinyl-2-caprolactam and 3-(tetrahydropyranyloxycarbonyl)-1-vinyl-6-butyl-2-caprolactam.

The synthesized monomers may be easily polymerized in ordinary radical polymerization techniques using radical polymerization initiators. By using the above-mentioned various monomers, homopolymers from the above-mentioned monomers and copolymers from the combinations which have an appropriate molar ratio in monomers, can be prepared. For copolymer, other monomers, such as 4-(t-butoxycarbonyloxy)-1-vinylcyclohexane, 3,5-(di-t-butoxycarbonyloxy)-1-vinylcyclohexane, 4-(tetrahydropyranyloxy)-1-vinylcyclohexane, 4-(tetrahydrofuranyloxy)-1-vinylcyclohexane, 3,5-(ditetrahydropyranyloxy)-1-vinylcyclohexane, 3,5-(ditetrahydrofuranyloxy)-1-vinylcyclohexane, t-butoxycarbonyloxystyrene, styrene and tetrahydropyranyloxystyrene, may be used.

These are polymerized in bulk polymerization or in a solution polymerization. For the solvent for polymerization, cyclohexanone, methylethylketone, benzene, toluene, dioxane, dimethylformamide alone or the combinations thereof may be used. Usually, the polymerization is carried out in the presence of a polymerization initiator, such as benzoylperoxide, 2,2'-azobisisobutyronitrile (AIBN), acetyl peroxide, lauryl peroxide, or t-butylperacetate.

In accordance with the present invention, polymers are provided and represented by the following general formulas (II) and (III):

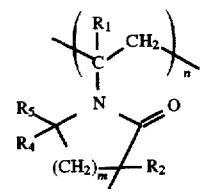

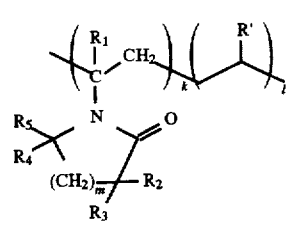

wherein, $R_1$ is hydrogen, an alkyl group containing 1 to 10 carbon atoms, an aryl group containing 6 to 12 carbon atoms or a trialkylsilyl group containing 3 to 9 carbon atoms;

$R_2$ represents —OR', —SO$_3$R', —CO$_2$R', —PO$_3$R', —SO$_2$R' or PO$_2$R', wherein R' is an alkyl group containing 1 to 10 carbon atoms, cycloalkyl group, a cyclo group containing a heteroatom such as N, O, P and S, or an aryl group containing 6 to 12 carbon atoms;

$R_3$ is hydrogen, an alkyl group containing 1 to 10 carbon atoms, an aryl group containing 6 to 12 carbon atoms, a trialkylsilyl group containing 3 to 9 carbon atoms or the same with $R_2$;

$R_4$ and $R_5$ is —OH, —OR, wherein R is an alkyl group containing 1 to 10 carbon atoms or an aryl group containing 6 to 12 carbon atoms, or the same with $R_1$;

R" is an aryl group containing 6 to 20 carbon atoms or represents an acrylate group —COOR'" wherein R'" is an alkyl group containing 1 to 10 carbon atoms or an aryl group containing 6 to 12 carbon atoms;

m is an integer of 0 to 10;

n is an integer of 10 to 10,000;

k is mole fraction ranging from 0.5 to 0.95; and 1 is mole fraction ranging from 0.05 to 0.5.

As seen in the general formulas, the polymers (II) are homopolymers resulting from one species of the aforementioned monomers or copolymers polymerizing the mixture of at least two kinds of N-vinyllactam monomers. The polymers (III) are copolymers from N-vinyllactam derivatives and styrene derivatives or vinylacrylate derivatives.

Among the prepared polymers, poly-3-(t-butoxycarbonyl)-1-vinyl-2-pyrrolidone (hereinafter referred to as "P(BCVP)") was found to be highly transparent as proven in the experiment in which a film 1 μm thick showed an optical absorbance of 0.05 or lower at deep uv range (200 to 300 nm). Thermal gravity analysis (hereinafter referred to as "TGA") showed that P(BCVP) was stable at up to 210° C. At higher than 210° C., rapid deprotection of t-butoxycarbonyl group occurs, producing 2-methylpropene and $CO_2$. In the presence of acid, the deprotection progresses in two steps.

First, the t-butyl group starts to secede from the backbone of the polymer at low temperature, e.g. 60° C. and completely breaks away at 100° C. Thereafter, $C_2$ is generated at 150° C. This fact informs us that P(BCVP) is far superior in thermal property by virtue of its high thermal decomposition temperature and is readily deprotected at low temperatures in the presence of acid. Differential scanning calorimetry (hereinafter referred to as "DSC") shows that the glass transition temperature of P(BCVP) ranges from 145° C. to 155° C. depending on the molecular weight thereof.

All of the polymers of N-vinyllactam derivatives, which are protected at the 3-position, show excellent film formability. Particularly, P(BCVP) and poly-3-(t-butoxycarbonyl)-1-vinyl-2-caprolactam (hereinafter referred to as "P(BCVC)"), which are both well dissolved in an organic solvent, such as dioxane, chloroform, tetrahydrofuran, cyclohexanone, 2-ethoxyethylacetate, acetone or methylethylketone. In contrast, the deprotected polymers are well dissolved in an alkali aqueous solution, such as sodium hydroxide or ammonium salts, but not in most of the organic solvents. This selective development before and after the deprotection of the t-butyl group endows the polymers with superior picture formability. In the case of P(BCVP), development can be accomplished even with only pure water. For other polymers including P(BCVC), a picture with high resolution can be obtained by developing the picture in a weak alkali aqueous solution. Of the polymers of the vinyllactam derivatives protected at 3-position, P(BCVP) and P(BCVC) were both found to be of high sensitivity, e.g. 1 mJ/cm², and show high contrast.

The solubilities of the representative polymers, P(BCVP) and P(BCVC), in various solvents are changed with the deprotection. A summary is shown in Table 1 below.

In the presence of acid, the deprotection of the t-butyl group was observed at 100° C. or lower in the films of such polymers. Ordinary experiments for fine picture formation confirmed that the polymers of the present invention could be applied for high sensitive chemical amplification resist. The thermal decomposition behavior analysis of the polymers was carried out in nitrogen atmosphere at a temperature elevation of 10° C./min by means of DSC, commercially available from DuPont company, identified as MODEL 2100, and of TGA:

TABLE 1

Solubility of P(BCVP) and P(BCVC) according to Deprotection

| Solvents | P(BCVP) | P(BCVC) | P(VPCA)* | P(VCCA)* |
|---|---|---|---|---|
| Acetone | ++ | ++ | − | − |
| Dioxane | ++ | ++ | + | + |
| Chloroform | ++ | ++ | − | − |
| Hexane | − | − | − | − |
| Tetrahydrofuran | ++ | ++ | + | + |
| Anisole | + | + | − | − |
| Cyclohexanone | ++ | ++ | + | + |
| 2-Ethoxyethylacetate | ++ | ++ | − | − |
| N,N-Dimethylformamide | ++ | ++ | + | + |
| Methylethylketone | ++ | ++ | + | + |
| 3.0 wt % NaOH sol'n | + | − | ++ | ++ |
| 2.38 wt % TMAH sol'n | + | − | ++ | ++ |
| pure Water | − | − | ++ | ++ |
| Methanol | + | + | + | + |
| Isopropanol | + | + | + | + |
| pure Water/MeOH (1/1) | + | ++ | + | + |

++ well dissolved, + a little dissolved, − not dissolved
P(VPCA): poly(1-vinyl-2-pyrrolidone-3-carboxylic acid
P(VCCA): poly(1-vinyl-2-caprolactam-3-carboxylic acid A better understanding of the present invention may be obtained in light of following examples which are set forth to illustrate, but are not to be construed to limit, the present invention.

EXAMPLE I

Synthesis of 3-(t-Butoxycarbonyl)-1-vinyl-2-pyrrolidinone

To a solution of diisopropylamine 14 ml (100 mmol) in tetrahydrofuran 40 ml free of moisture, 40 ml (100 mmol) of 2.5M n-butyllithium was added, and the resulting solution was stirred at −78° C. for 30 min and allowed to react until the temperature was elevated up to room temperature. After being frozen down to −78° C., 11.1 g (100 mmol) of N-vinylpyrrolidinone was added to the solution and subjected to reaction, at the same temperature for 30 min. Thereafter, 24 g (110 mmol) of di(t-butyl)dicarbonate was added dropwise, followed by the reaction at −78° C. for 2 hours. This reaction was diluted with diethylether and washed many times with pure water. The organic solvent of the organic phase was distilled and the residue was subjected to silica gel column chromatography, to obtain 15 g of pure 3-(t-butoxycarbonyl)-1-vinyl-2-pyrrolidinone (hereinafter referred to as "BCVP"). Its chemical structure was determined by IR spectra and NMR.

EXAMPLE II

Synthesis of 3-(t-Butoxycarbonyl)-1-vinyl-2-caprolactam 17.2 g of pure 3-(t-butoxycarbonyl)-1-vinyl-2-caprolactam (hereinafter referred to as "BCVC") was synthesized in a similar manner to that of Example I, except for using 13.9 g (100 mmol) of N-vinylcaprolactam instead of N-vinylpyrrolidinone. IR spectra and NMR analysis were taken to determine the chemical structure of BCVC synthesized.

EXAMPLE III

Synthesis of 3-(Tetrahydropyranyloxycarbonyl)-1-vinyl-2-pyrrolidinone 10.6 g (0.05 mol) of the BCVP synthesized in Example I was dissolved in 50 ml of tetrahydrofuran free of moisture.

To this solution, 4.3 g (0.05 mol) of tetrahydropyran and 0.3 g of p-toluene sulfonic acid was added, and allowed to react at 0° C. for 4 hours. The reaction was diluted with diethylether and washed several times with pure water. The organic solvent of the organic phase was distilled and the residue was subjected to silica gel column chromatography, to obtain 9.8 g of pure 3-(tetrahydropyranyloxycarbonyl)-1-vinyl-2-pyrrolidinone (hereinafter referred to as "TPVP"). The chemical structure of the resulting TPVP was determined by IR spectra and NMR.

EXAMPLE IV

Synthesis of 3-(Tetrahydrofuranyloxycarbonyl)-1-vinyl-2-pyrrolidinone 8.9 g of N-vinyl-2-pyrrolidinone-3-sodium carbonate was dissolved in 50 ml of tetrahydrofuran free of moisture. To this solution, 7 ml of triethylamine and 5.3 g of 2-chlorotetrahydrofuran were added and allowed to react at room temperature for 1 hours. This reaction was diluted with diethylether and washed several times with pure water. The organic solvent of the organic phase was distilled and the residue was subjected to silica gel column chromatography, to obtain 9.3 g of pure 3-(tetrahydrofuranyloxycarbonyl)-1-vinyl-2-pyrrolidinone (hereinafter referred to as "TFVP"). Its chemical structure was determined by IR spectra and NMR.

EXAMPLE V

Synthesis of 3-(Tetrahydropyranyloxycarbonyl)-1-vinyl-2-caprolactam 10.7 g of pure 3-(tetrahydropyranyloxycarbonyl)-1-vinyl-2-caprolactam (hereinafter referred to as "TPVC") was synthesized in a similar manner to that of Example III, except that 6.7 g of N-vinylcaprolactam was used instead of BCVP.

IR spectra and NMR analysis were taken to determine the chemical structure of TVPC synthesized.

EXAMPLE VI

Synthesis of 3-(Tetrahydrofuranyloxycarbonyl)-1-vinyl-2-caprolactam 10.8 g of pure 3-(tetrahydrofuranyloxycarbonyl)-1-vinyl-2-caprolactam (hereinafter referred to as "TFVC") was synthesized in a similar manner to that of Example IV, except that 10.3 g of N-vinyl-2-caprolactam-3-sodiumcarbonate was used instead of N-vinyl-2-pyrrolidinone-3-sodium carbonate. IR spectra and NMR analysis were taken to determine the chemical structure of TFVC synthesized.

EXAMPLE VII

Synthesis of BCVP Polymer 2.1 g of BCVP monomer synthesized in Example I was dissolved in a pure or mixed solvent and placed in a polymerization glass ample. The reactant was polymerized at 70° C. for 6 hours under vacuum in the presence of AIBN, a polymerization initiator. The reaction product was precipitated in petroleum ether and the precipitate was dried to give 1.8 g of polymer, P(BCVP): Conversion yield 80%. Its inherent viscosity was observed to vary with the solvents which were used, but determined in the state of cyclohexanone solution of 0.5 g/dl at 25° C. by use of a glass viscosity tube. The results are shown in Table 2 below.

TABLE 2

Physical Properties of P(BCVP) in Various Solvents

| Solvent[a] | AIBN[b] (mol %) | M/S[c] (g/ml) | Time (hr) | Conversion Yield (%) | Inherent Viscosity (dl/g) | Tg[d] (°C.) |
|---|---|---|---|---|---|---|
| A | 1 | 1 | 10 | 89 | <0.10 | — |
| B | 1 | 1 | 5 | 89 | 0.12 | — |
| C | 1 | 1 | 10 | 91 | 0.18 | 143 |
| D | 0.5 | 1 | 5 | 90 | 0.20 | 151 |
| E | 0.5 | 1 | 6 | 91 | 0.30 | 152 |
| F | 0.5 | 1 | 7 | 90 | 0.77 | 155 |

[a]A methyethylketone, B cyclohexanone, C dioxane/cyclohexanone (3/1 volume ratio), D dioxane/cyclohexanone (5/1 volume ratio), E dioxane/cyclohexanone (10/1 volume ratio), F dioxane
[b]mol % based on the monomer
[c]ratio of solvent volume to the total weight of monomer
[d]glass transition temperature

EXAMPLES VIII THROUGH XII

Synthesis of BCVC, TPVP, TFVP, TPVC and TFVC polymers

Polymers, P(BCVC), P(TPVP), P(TFVP), P(TPVC) and P(TFVC) were prepared with the same procedure that was used in Example VII, using monomers, BCVC, TPVP, TFVP, TPVC and TFVC, synthesized in Examples II through VI, respectively.

EXAMPLE XIII

Preparation of Resist Sol'n and Formation of Positive Fine Picture (I)

10 to 30% by weight of P(BCVP) was dissolved in cyclohexanone. In this solution, an onium salt or organic sulfonic acid, acting as a photoacid generator, was added at an amount of 5 to 30% by weight based on the weight of the resist polymer. Filtration with a ultrafine filter gave a chemical amplification resist solution. Subsequently, it was spin-coated on a silicon wafer, to form a thin film with a thickness of about 1.0 µm. This wafer was pre-baked for 1 to 5 minutes in an oven or hot plate heated to 120° C., exposed to the light radiated from a deep uv stepper or excimer laser stepper, subjected to post exposure-baking (PEB) for 1 to 5 minutes in an oven or hot plate heated from to 120 °to 140° C. and immersed in pure water for 90 seconds for development. As a result, a positive resist picture of submicrons was obtained.

EXAMPLE XIV

Preparation of Resist Sol'n and Formation of Positive Fine Picture (II)

Using P(BCVC), the procedure of Example XIII was repeated to obtain a resist solution. Immersion in 0.8 wt % TMAH aqueous solution for 90 seconds gave a positive resist picture of submicrons.

As described and proven hereinbefore, the novel N-vinyllactam derivatives of the present invention are materials for homopolymers copolymers for use as chemical amplification resist suitable for deep uv. In addition, the photoresist made of the polymers according to the present invention is of high sensitivity so that pictures can be formed with high resolution. Therefore, the radiation-sensitive polymers can be applied for highly integrated semiconductor devices and electron device lithography. Consequently, ultrafine circuits can be formed and an exceptional improvement in pattern formation can be attained by using the photoresist prepared according to the present invention.

The present invention has been described in an illustrative manner, and it is to be understood that the terminology being used is intended to be in the nature of description rather than of limitation.

Many modifications and variations of the present invention are possible in light of the above teachings. Therefore, it is to be understood that within the scope of the appended claims, the invention may be practiced in ways other than those specifically described.

What is claimed is:

1. N-vinyllactam derivatives, represented by the following general formula (I):

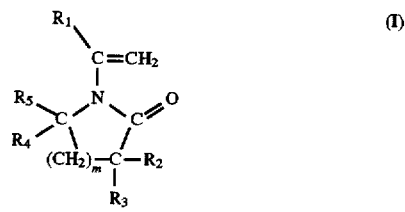

wherein, $R_1$ is hydrogen, an alkyl group containing 1 to 10 carbon atoms or a trialkylsilyl group containing 3 to 9 carbon atoms;

$R_2$ represents —OR', —SO$_3$R', —CO$_2$R', —PO$_3$R', —SO$_2$R' or —PO$_2$R', wherein R' is an alkyl group containing 1 to 10 carbon atoms, cycloalkyl group containing 3 to 9 carbon atoms, a cyclo group containing a ring heteroatom such as N, O, P and S, or an aryl group containing 6 to 12 carbon atoms;

$R_3$ is hydrogen, an alkyl group containing 1 to 10 carbon atoms, an aryl group containing 6 to 12 carbon atoms, a trialkylsilyl group containing 3 to 9 carbon atoms, or $R_3$ is the same as $R_2$;

$R_4$ and $R_5$ is —OH, —OR, wherein R is an alkyl group containing 1 to 10 carbon atoms or an aryl group containing 6 to 12 carbon atoms, or R is the same as $R_1$; and m is an integer of 0 to 10.

2. The derivatives of claim 1 wherein $R_1$ is hydrogen, an alkyl group containing 1 to 10 carbon atoms, or a trialkylsilyl group containing 3 to 9 carbon atoms.

* * * * *

UNITED STATES PATENT AND TRADEMARK OFFICE
CERTIFICATE OF CORRECTION

PATENT NO. : 5,750,680

DATED : 05/12/98

INVENTOR(S) : Jin B. Kim

It is certified that error appears in the above-identified patent and that said Letters Patent is hereby corrected as shown below:

Column 3, line 20, delete the structural formula for Formula (I) and substitute therefore:

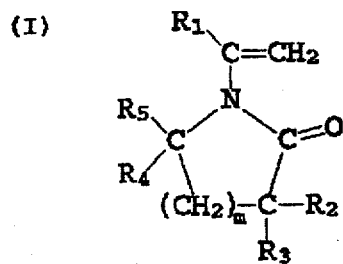

UNITED STATES PATENT AND TRADEMARK OFFICE
CERTIFICATE OF CORRECTION

PATENT NO. : 5,750,680
DATED : 05/12/98
INVENTOR(S) : Jin B. Kim

It is certified that error appears in the above-identified patent and that said Letters Patent is hereby corrected as shown below:

Column 4, line 28, delete the structural formula for Formula (II) and substitute therefore:

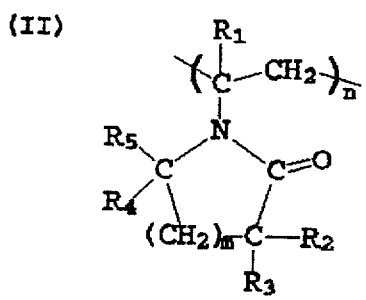

UNITED STATES PATENT AND TRADEMARK OFFICE
CERTIFICATE OF CORRECTION

PATENT NO. : 5,750,680

DATED : 05/12/98

INVENTOR(S) : Jin B. Kim

It is certified that error appears in the above-identified patent and that said Letters Patent is hereby corrected as shown below:

Column 4, line 35, delete the structural formula for Formula (III) and substitute therefore:

(III)

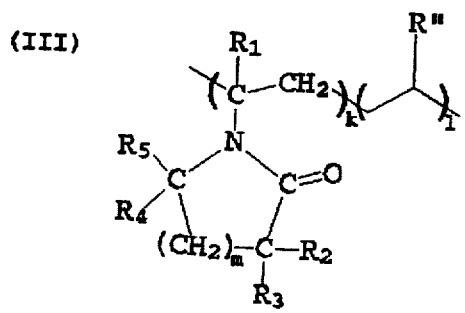

Signed and Sealed this

Sixteenth Day of February, 1999

Attest:

*Attesting Officer*

*Acting Commissioner of Patents and Trademarks*